United States Patent [19]

Hevey et al.

[11] 4,228,237

[45] Oct. 14, 1980

[54] METHODS FOR THE DETECTION AND DETERMINATION OF LIGANDS

[75] Inventors: Richard C. Hevey, Rockport, Me.; Mark K. Malmros, Newton, Pa.

[73] Assignee: Calbiochem-Behring Corp., La Jolla, Calif.

[21] Appl. No.: 944,254

[22] Filed: Sep. 21, 1978

[51] Int. Cl.$^2$ .............................................. C12Q 1/66
[52] U.S. Cl. .................................... 435/7; 23/230 B; 424/12; 435/188
[58] Field of Search .......................... 435/7, 188, 177; 424/12; 23/230 B

[56] References Cited

U.S. PATENT DOCUMENTS

| | | | |
|---|---|---|---|
| 4,002,532 | 1/1977 | Weltman et al. | 435/7 |
| 4,016,043 | 4/1977 | Schums et al. | 435/7 |
| 4,134,792 | 1/1979 | Boguslnski et al. | 435/7 |

FOREIGN PATENT DOCUMENTS

841179  8/1976  Belgium ...................................... 435/7

OTHER PUBLICATIONS

May, et al., "N$\epsilon^{B29}$-(+)-Biothylinsulin and its Complexes with Audin", J. Biol Chem., vol. 253, No. 3, (1978) pp. 686–690.

Manning, et al., "A Method for Gene Enrichment Based on the Auidin-Biochem Interaction Application to the *Drosophilia* Ribosomul Genes," *Biochem.*, vol. 16, No. 7 (1977), pp. 1364–1370.

Heggeness, et al., "Use of the Avidin-Biotin Complex for the Localization of Actin and Myosin with Fluorescene Microscopy," *J. Cell Biol.* vol. 73 (1977), pp. 783–788.

Hofmann, et al., "Avidin-Biotin Affinity Columns, General Methods for Attaching Biotin to Peptides and Proteins," *J. Am. Chem. Soc.* vol. 100, No. 11 (1978), pp. 3585–3590.

Bayer, et al., "Preparation of Ferritin-Avidin Conjugates by Reductive Alkylation for Use in Electron Microscope Cytochemistry," *J. Histochem and Cytochem*, vol. 24, No. 8, (1976), pp. 933–939.

Wisdom, "Enzyme-Immunoassay," *Clin. Chem.*, vol. 22 No. 8, (1976), pp. 1243–1255.

*Primary Examiner*—Thomas G. Wiseman
*Attorney, Agent, or Firm*—Natalie Jensen

[57] ABSTRACT

A method for determining the presence of a ligand in a liquid medium which utilizes enzyme labeled avidin and biotin labeled reagent in a specific binding process wherein the ligand to be detected is contacted with an insoluble phase containing specific binding substance for the ligand. Various protocols may be used to assay the resulting enzyme activity which is related to the amount of ligand in the liquid medium.

28 Claims, No Drawings

METHODS FOR THE DETECTION AND DETERMINATION OF LIGANDS

SUMMARY OF INVENTION

The present invention relates to a method for the determination of a ligand in a liquid medium. More specifically, the invention relates to a method which utilizes a biotinavidin system in ligand determination.

According to the present invention, an enzyme is covalently coupled to avidin and the resulting enzyme labeled avidin is then reacted with biotin labeled reagent (i.e., biotin labeled ligand or biotin labeled specific binding substance for said ligand) prior to or during utilization of the latter in a specific binding reaction. The basic components in the binding reaction are, in addition to the biotin labeled reagent, liquid medium or sample (presumed to contain the ligand to be detected) and an insoluble phase containing a specific binding substance for said ligand. The biotin labeled reagent may be bound to enzyme labeled avidin after it has reacted with the insoluble phase or, alternatively, the biotin labeled reagent may be pre-reacted with enzyme labeled avidin and the resulting conjugate used directly.

Following the specific binding reaction, the enzyme activity of either the insoluble phase or the liquid phase is determined by a suitable detection reaction system; the amount of activity being related to the quantity of ligand in the sample.

Ligand analysis performed according to the instance invention can be accomplished with the aid of either a noncompetitive binding reaction or a competitive binding reaction.

Accordingly, a first aspect of the present invention relates to a method for determining the presence and amount of a ligand in a liquid medium suspected of containing same, which method comprises providing an insoluble phase containing a specific binding substance for the ligand; incubating the insoluble phase with the following reagents:
  (i) a measured amount of liquid medium suspected of containing the ligand;
  (ii) biotin labeled specific binding substance for the ligand; and
  (iii) enzyme labeled avidin; separating unreacted reagents from the insoluble phase after incubation and determining the enzyme activity of either the insoluble phase or the separated unreacted reagent whereby the activity is related to the amount of ligand in the liquid medium.

Another aspect of the present invention relates to a method for determining the presence and amount of a ligand in a liquid medium suspected of containing same, which method comprises providing an insoluble phase containing a specific binding substance for the ligand; incubating the insoluble phase with the following reagents;
  (i) a measured amount of liquid medium suspected of containing the ligand;
  (ii) biotin labeled specific binding substance for the ligand bound to enzyme labeled avidin; separating unreacted reagents from the insoluble phase after incubation and determining the enzyme activity of either the insoluble phase or the separated unreacted reagent whereby the activity is related to the amount of ligand in the liquid medium.

Still another aspect of the present invention relates to a method for determining the presence and amount of a ligand in a liquid medium suspected of containing same, which method comprises providing an insoluble phase containing a specific binding substance for the ligand; incubating the insoluble phase with the following reagents:
  (i) (A) a reagent comprising a measured amount of liquid medium suspected of containing the ligand and (B) a known quantity of biotin labeled ligand; and
  (ii) enzyme labeled avidin; separating unreacted reagents from the insoluble phase after incubation and determining the enzyme activity of either the insoluble phase or the separated unreacted reagent whereby the activity is related to the amount of ligand in the liquid medium.

A still further aspect of the present invention relates to a method for determining the presence and amount of a ligand in a liquid medium suspected of containing same, which method comprises providing an insoluble phase containing a specific binding substance for the ligand; incubating the insoluble phase with a reagent comprising (A) a measured amount of liquid medium suspected of containing the ligand and (B) a known quantity of biotin labeled ligand bound to enzyme labeled avidin; separating unreacted reagent from the insoluble phase after incubation; and determining the enzyme activity of either the insoluble phase or the separated unreacted reagent whereby the activity is related to the amount of ligand in the liquid medium.

DETAILED DESCRIPTION OF THE INVENTION

Although the biotin-avidin system of the present invention may be utilized in any conventional heterogeneous binding process, non-competitive and competitive binding processes are preferred.

Generally, the components of the specific binding reaction (the insoluble phase containing a specific binding substance for the ligand and the appropriate reagents) may be mixed together in desired manner or sequence provided that the resultant enzyme activity is easily measurable in a subsequent detection reaction system.

A particularly preferred non-competitive binding process is the "Sandwich" technique wherein the components of the binding reaction comprise an insoluble phase containing a specific binding substance for the ligand and the following reagents:
  (i) a measured amount of liquid medium suspected of containing the ligand;
  (ii) biotin labeled specific binding substance for the ligand; and
  (iii) enzyme labeled avidin.

In an alternative mode, biotin labeled specific binding substance for the ligand bound to enzyme labeled avidin may be used in lieu of reagents (ii) and (iii).

In the non-competitive binding process, the insoluble phase may be incubated with the reagents in the presence of one another, or alternatively the insoluble phase may be incubated with the reagents individually in particular sequence. The latter method is preferred.

When the insoluble phase is incubated with individual reagents in particular sequence, the binding process can be effected in either two or three incubation periods.

In the three step incubation process, the insoluble phase is first reacted with the ligand reagent, i.e., a measured amount of liquid medium suspected of containing the ligand. Unreacted reagent is then removed and biotin labeled specific binding substance for the ligand is added. Following the reaction of the biotin labeled specific binding substance, unreacted biotin labeled reagent is removed and enzyme labeled avidin is added. Following the reaction of enzyme labeled avidin, unreacted reagent is separated from the insoluble phase and the enzyme activity of either the insoluble phase or the separated unreacted enzyme labeled avidin is determined by a suitable detection reaction. The enzymatic activity of the insoluble phase is directly related to the amount of ligand in the liquid medium whereas the enzymatic activity of separated unreacted enzyme labeled avidin is inversely related to the amount of ligand.

When biotin labeled specific binding substance is prereacted with enzyme labeled avidin, the binding process can be effected in two steps by substituting the biotin labeled reagent bound to enzyme labeled avidin for the individual biotin labeled and enzyme labeled avidin reagents.

In order to obtain quantitative results in the foregoing non-competitive binding process, the quantity of insoluble phase mixed with the reagents is generally larger than that quantity which is capable of forming bonds with the total amount of ligand assumed to be in the liquid medium. The quantity, in practice, is chosen in conformity with the aforementioned criteria based on the assumption that the ligand is present in the liquid at the highest concentration possible. The non-competitive process differs from conventional radioimmunoassay (RIA) in that in the first instance, the ligand to be determined is assayed directly by reaction with excess labeled binding substance whereas in the second instance, the ligand to be determined is in competition with labeled ligand for a limited amount of binding substance. Non-competitive binding is particularly suited to the detection of high molecular weight ligands.

If a competitive binding process is used, the components of the binding reaction comprise an insoluble phase containing a specific binding substance for the ligand and the following reagents:
  (i) (A) a measured amount of liquid medium suspected of containing the ligand and (B) a known quantity of biotin labeled ligand; and
  (ii) enzyme labeled avidin.
In an alternative mode, (B) may be biotin labeled ligand bound to enzyme labeled avidin thereby eliminating the need for reagent (ii).

In a competitive binding assay employing reagents (i) and (ii), the insoluble phase may be incubated with the reagents in the presence of one another, or alternatively the insoluble phase may be incubated with the reagents individually in particular sequence. In the latter preferred mode, the insoluble phase is first incubated with a reagent comprising (A) a measured amount of liquid medium suspected of containing the ligand and (B) a known quantity of biotin labeled ligand. A competition is established between the ligand to be determined and biotin labeled ligand for the binding sites of the insolubilized specific binding substance. After equilibration, unreacted reagent is removed and enzyme labeled avidin reagent is added. Following the reaction of the enzyme labeled avidin reagent, unreacted reagent is separated from the insoluble phase and the enzyme activity of either the insoluble phase or the separated unreacted enzyme labeled avidin is determined by a suitable detection reaction. The enzyme activity of the insoluble phase is inversely related to the amount of ligand in the liquid medium, whereas the enzyme activity of the separated unreacted enzyme labeled avidin is directly related to the amount of ligand.

When biotin labeled ligand is pre-reacted with enzyme labeled avidin, the binding process can be effected in one incubation period by simply incubating the insoluble phase with a reagent comprising (A) a measured amount of liquid medium suspected of containing the ligand and (B) a known quantity of biotin labeled ligand bound to enzyme labeled avidin.

In order to obtain quantitative results in the competitive binding process, the quantity of insoluble phase mixed with the reagent(s) is usually less than that amount which is capable of forming bonds with the total quantity of ligand presumed to be present in the liquid; and less than the total quantity of biotin labeled ligand or biotin labeled ligand bound to enzyme labeled avidin. In practical applications, this quantity is selected to correspond to the aformentioned criteria, based on the assumption that the largest quantity of ligand which can be present in the liquid medium is indeed there. In general, the quantity of biotin labeled ligand or biotin labeled ligand bound to enzyme labeled avidin which is brought in contact with the liquid medium does not exceed the smallest quantity of ligand to be determined in the liquid medium. The competitive binding method is especially suitable for detecting ligands which have specific binding substances larger than themselves.

Ligands which may be determined according to the instant invention are specific organic materials for which specific binding substances can be provided. A specific binding substance is any substance or group of substances having a specific binding affinity for the ligand to the exclusion of other substances. When a non-competitive process is employed, specific binding substance contained in the insoluble phase and specific binding substance bound to biotin may be identical or such substances may differ as in the rubella antibody assay (discussed infra).

Generic classes of materials embraced by the term ligand include, for example, antigens, antibodies and haptens as well as those substances having naturally occurring receptors in a living organism.

When the ligand is an antigen, specific binding substance utilized to detect the antigen is normally the corresponding antibody produced when the antigen is introduced into the blood stream of a vertibrate. Examples of antigens which may be determined according to the instant invention include, for example, polypeptide and protein hormones, human IgE and alpha$_1$ fetoprotein, a fetal antigen that also occurs in serum of patients with hepatoma and embryonal adrenocarcinoma. Conversely, when the ligand is an antibody the eliciting antigen may be employed as a specific binding substance. Assay of antibody titers is particularly useful in the diagnosis of, for example, infectious diseases such as syphilus, rubella and infection caused by haemolytic streptococci.

When the ligand is a hapten (i.e., a protein-free substance which does not itself elicit antibody formation), specific binding substance utilized to detect the hapten is an antibody produced when the hapten, bound to an antigenic carrier, is introduced into the blood stream of a vertebrate. Examples of haptens which may be determined according to the instant invention include steriods such as estrone, estradiol, testosterone, pregnanediol and progesterone; vitamins such as $B_{12}$ and folic acid; triodothyronine, thyroxine, histamine, serotonine, digoxin, prostaglandins, adrenalin, noradrenalin, morphine, vegetable harmones and antibiotics such as penicillin.

When the ligand is a substance having a naturally occurring receptor, the receptor can be utilized as the specific binding substance for detecting the ligand, provided the receptor can be isolated in a form specific for the ligand. Illustrative ligands which have naturally occurring receptors include thyroxine, many steriods, polypeptides such as insulin and angiotensin and many others. Receptors for this class of ligands are usually proteins or nucleic acids.

Ligands which are determined according to the instant invention with the aid of a non-competitive binding process (i.e., the "Sandwich" technique) must have at least two reactive sites in order to bind with both the insoluble phase containing specific binding substance and biotin labeled specific binding substance. The foregoing criteria is not necessary when a competitive binding process is employed.

Preparation of the biotin labeled reagent (i.e., biotin labeled specific binding substance or biotin labeled ligand) may be accomplished by simply mixing the entity to be labeled with biotin N-hydroxysuccinimide ester (BNHS) in a suitable solvent such as dimethylformamide. Although the use of BNHS is preferred, other suitable reagents and/or methods may be employed.

Preparation of the insoluble phase containing specific binding substance for the ligand to be determined can be accomplished by known methods. For example, the specific binding substance can be attached to a solid carrier by cross-linking, by covalent binding or by physical coupling. Examples of solid carriers used in the instant invention include polypropylene tubes, polystyrene microtiter plates and nylon beads. When the ligand to be detected is an antigen, preparation of the insoluble phase can be accomplished by simply coating the tubes or plates with the appropriate antibody. When nylon beads are used, the appropriate antibody may be covalently coupled to the beads by the method of Faulstich et al described in FEBS Letters, 48, 226, (1974).

Although a wide variety of enzymes can be used to prepare the enzyme labeled avidin reagent, certain enzymes are preferred. For example, in qualitative determination of a ligand, the enzyme should preferably be detected by a color reaction.

Enzymes suitable for use in the instant invention include those classified as oxidoreductases, hydrolases and lyases according to the International Union of Biochemists (I.U.B.). Of the oxidoreductases, those acting on the CHOH group, the aldehyde or keto group or the $CHNH_2$ group of donors (1.1, 1.2 and 1.4 respectively) and those acting on hydrogen peroxide as acceptor (1.11) are preferred. Particularly preferred oxidoreductases include, for example, glucose oxidase and horseradish peroxidase. Of the hydrolases, of particular interest are those acting on ester bonds (both organic and inorganic esters) and those acting on glycosyl compounds, particularly glycoside hydrolases, namely 3.1 and 3.2 respectively. Particularly preferred hydrolases include, for example, alkaline phosphatase and β-galactosidase.

The enzyme labeled avidin reagent of the instant invention prepared by covalent coupling of the selected enzyme to avidin. This covalent linking can be achieved by direct condensation of existing linking groups or by the addition of external bridging molecules. For example, horseradish peroxidase (HRP) is a glycoprotein having a carbohydrate portion which is not required for enzymatic activity and which can be used for the formation of aldehyde groups by oxidation with sodium m-periodate. Blocking of α- and γ-amino groups and hydroxy groups of HRP with fluorodinitrobenzene prior to oxidation prevents self-coupling and allows the HRP-aldehyde to condense with available amino groups present in avidin. Moreover, alkaline phosphatase can be coupled to avidin by the condensation of free amino groups in the foregoing molecules with aldehyde groups provided by the external bridging molecule glutaraldehyde.

Many bivalent and polyvalent bridging molecules, useful in coupling protein molecules, have been reported in the literature. Illustrative examples, in addition to glutaraldehyde, include carbodiimides, diisocyanates and p,p' difluoro-m,m'-dinitrodiphenylsulphone.

The determination of enzyme activity in the instant invention is accomplished with a detection reaction system suitable for the particular enzyme employed. Since there are differences, not only between assays for different enzymes, but even in the variety of assays for a particular enzyme, no general description of the assay techniques can be given; however, a wide diversity of media, conditions and substrates suitable for enzymes employed herein can be found in Bergmeyer, Methods of Enzymatic Analysis, Academic Press, New York, 1965.

The liquied medium which is presumed to contain the ligand to be determined may be a natural or synthetic liquid. In many instances, the liquid will be a biological fluid. Biological fluids which are examinable for ligands according to the instant invention include, for example, serum, plasma, urine, amniotic fluid and cerebrospinal fluid. Ligands may also be determined by dissolution of the ligand in appropriate non-aqueous media.

DESCRIPTION OF SPECIFIC EMBODIMENTS

The following specific description is given to enable those skilled in the art to more clearly understand and practice the present invention. It should not be considered as a limitation upon the scope of the invention but merely as being illustrative and representative thereof.

EXAMPLE I

A general procedure for the purification of antibodies is described below.

The gamma globulin (IgG) fraction of the appropriate rabbit antiserum is purified by the slow dropwise addition of 50 ml of saturated ammonium sulfate solution (adjusted to pH 7.8 with 1 N $NH_4OH$) to 100 ml of the serum at room temperature under constant stirring. The precipitated serum is stirred for two hours at room temperature and then held at 4° C. overnight. Thereafter the precipitate is pelleted by centrifugation at 10,000 G for 20 minutes. The supernatant is decanted and the pellet is resuspended in approximately 25 ml of 0.01 M borate buffered saline pH 8.5 and then dialysed against 10 liters of the same buffer for 72 hours at 4° C. Thereafter the protein solution is dialysed for 4–6 hours against four liters of 0.01 M sodium phosphate buffer pH 7.5 and then chromatographed on DEAE cellulose (Whatman DE-52) equilibrated in the same buffer. The protein-rich fractions are pooled and dialysed for 16 hours against two-eight liter changes of borate buffered saline pH 8.5. The antibody fraction is concentrated by ultrafiltration to 4–6 mg/ml and stored frozen at −75° C. with 0.01% sodium azide.

EXAMPLE II

Biotinyl-N-hydroxysuccinimide ester is prepared according to the following procedure.

Dicyclohexyl carbodiimide (0.8 g, 4 m Moles) is added to a solution of biotin (1 g, 4 m Moles) and N-hydroxy-succinimide (0.6 g, 5.2 m Moles) in 12 ml of dimethylformamide. The suspension is stirred and the reaction allowed to proceed for 20–24 hours. Thereafter the precipitate is removed by filtration and the filtrate is maintained at 0° C. overnight. Any additional precipitate is removed by filtration and the resulting filtrate is evaporated under reduced pressure. The residue is washed extensively with ether and recrystalized twice from isopropanol to yield a product having a m.p. of 216°–218° C. The crystals are stored desicated at 4° C.

EXAMPLE III

A general procedure for the preparation of biotin labeled reagent is described below.

The purified IgG fraction, prepared according to Example I, is adjusted to 4 mg/ml in borate buffered saline pH 8.5. Thereafter, biotinyl-N-hydroxysuccinimide ester dissolved in dimethylformamide (10 mg/ml) is added to the antibody solution at a volume of 50 µl/ml. The extent of biotin labeling can be adjusted by the volume of biotinyl-N-hydroxysuccinimide ester added. The reaction mixture is stirred at room temperature for two hours and then dialysed overnight against 1 liter (per ml) of 0.05 M sodium phosphate buffered saline pH 7.4 at 4° C. The resulting reagent is stored at 4° C. in the present of sodium azide.

Human gamma globulin (IgG) is labeled with biotin according to the above procedure, i.e., an ammonium sulfate precipitated human IgG fraction (stored frozen at −20° C.; 16% protein) is diluted to 4 mgIgG/ml in phosphate buffered saline and then labeled as described.

EXAMPLE IV

Avidin is conjugated to horseradish peroxidase (HRP) according to the following procedure.

HRP (10 mg) is dissolved in 2.0 ml of 0.3 M sodium bicarbonate and the solution is then dialysed overnight at 4° C. against two liters of 0.3 M sodium bicarbonate. Thereafter, 0.2 ml of 1% flurodinitrobenzene in absolute ethanol is added to the HRP solution and gentle mixing is carried out at room temperature. After 1 hour, 2 ml of 0.06 M sodium periodate in distilled water is added and the solution is gently mixed for an additional 30 minutes whereupon a brown to dark green color can be observed. Ethylene glycol (2 ml of 0.16 M in water) is then added to the reaction mixture and gentle stirring is continued for 1 hour. The solution is then dialysed overnight at 4° C. against four liters of 0.01 M sodium carbonate buffer pH 9.5. Five ml of the enzyme solution is recovered after dialysis. Chromatographically purified avidin (8 mg), dissolved in one ml of 0.01 M sodium carbonate buffer, pH 9.5, is added to the peroxidase solution and gentle stirring is carried out for three hours at room temperature.

To the above obtained avidin peroxidase solution is added 5 mg of sodium borohydride and the solution is then held overnight at 4° C. The solution is then dialysed over the weekend at 4° C. against 0.05 M sodium phosphate buffered saline pH 7.1. The HRP labeled avidin is purified by column chromatography on G-150 Sephadex equilibrated with 0.05 M sodium phosphate buffered saline pH 7.1. The fractions containing labeled avidin are pooled and concentrated to approximately 0.5 mg/ml subsequent to sterile filtration for storage.

EXAMPLE V

The method of coupling alkaline phosphatase to avidin with glutaraldehyde is accomplished according to the following procedure.

Five mg of alkaline phosphatase in one ml of an ammonium sulfate suspension is dialysed for 5 hours at 4° C. against 3 liters of 0.1 M sodium phosphate, pH 6.8. Purified avidin (12 mg) is gently dissolved in the alkaline phosphatase solution. While the solution is gently stirred, 0.05 ml of a 1% aqueous glutaraldehyde solution is added in 0.01 ml aliquots over a 30 minute period. The reaction mixture is stirred for 2 hours at room temperature and then dialysed for 48 hours at 4° C. against 10 liters of 0.05 M sodium phosphate buffered saline pH 7.5. The resulting dialysate is stored at 4° C. in the presence of sodium azide.

EXAMPLE VI

Preparation of suitable solid phase immuno-adsorbents containing specific binding substances is illustrated below.

Polypropylene tubes, 12×75 mm, are coated with 30 µg/ml of the appropriate rabbit antibody in 0.1 M sodium carbonate buffer pH 9.8 (300 µl per tube), and stored overnight at 4° C. Prior to use, the tubes are washed with 0.9% NaCl containing 0.05% Tween-20.

Polystyrene microtiter plates are coated with antibody by the same method employed for coating the polypropylene tubes.

Nylon beads are coated with rabbit IgG specific for human IgE or human alpha$_1$ fetoprotein by covalent coupling according to the procedure described by Faulstich et al in FEBS Letters, 48, 226 (1974).

EXAMPLE VII

A general procedure for the determination of a ligand antigen using the "Sandwich" technique is described below.

Antibody coated polypropylene tubes (12 mm×75 mm) are washed three times with 0.9% NaCl containing 0.5% Tween-20 prior to use. To each tube, 200 µl of appropriately diluted (1) antigen standard or (2) unknown sample is added. The tubes are capped and incubated at room temperature for 3 hours. Thereafter the tubes are aspirated and then washed 3 times with NaCl-Tween-20. To each tubes, 200 µl of the appropriately diluted biotin labeled antibody is added and the tubes are incubated overnight at 4° C. The tubes are then aspirated and washed 3 times with NaCl-Tween-20 solution. To each tube, 200 µl of an appropriate dilution of HRP labeled avidin is added. The tubes are held at room temperature for 5–60 minutes, aspirated and then washed 3 times with NaCl-Tween-20.

The enzyme activity in the insoluble phase is determined by adding 1 ml of 0.033 M sodium phosphate buffer pH 6.6 containing 5.4 mM o-phenylenediamine dihydrochloride and 0.03% $H_2O_2$ to each tube at timed intervals.

When the color intensity is considered suitable (15 to 30 minutes), the enzymatic reaction is terminated and the absorbance is measured at an appropriate wavelength.

When alkaline phosphatase labeled avidin is used in lieu of HRP-labeled avidin, enzyme activity in the insoluble phase is determined by adding 1 ml of 0.05 M sodium carbonate buffer, pH 9.8 containing 1 mg/ml p-nitrophenylphosphate and 1 mM mgCl$_2$. Following an appropriate incubation period, the reaction is terminated with 100 μl of 1 N NaOH and the absorbence at 400 nm is determined.

Enzyme immunoassays conducted in microtiter plates are performed in essentially the same manner as described above. The enzyme assays are conducted using only 250 μl of the substrate solution and terminated with 50 μl of 1 N NaOH. The color intensity is estimated qualitatively, or determined quantitatively by transferring the solution to a 250 μl microcuvette and reading spectrophotometrically.

Enzyme immunoassays using antibody coated nylon beads are carried out by placing the beads in 12 mm×75 mm glass culture tubes. All reagent volumes are increased to 0.4 ml. The enzyme assays are conducted with 1 ml of the assay solution as described above.

EXAMPLE VIII

Repeating the procedure of Example VII, but replacing biotin labeled antibody and HRP labeled avidin with biotin labeled antibody bound to HRP labeled avidin, affords a procedure wherein the number of incubation periods required is reduced from three to two.

HRP labeled avidin is pre-reacted with biotin labeled antibody by simply mixing a suitable dilution of the appropriate biotin labeled antibody and a suitable dilution of HRP labeled avidin. The resulting complex is added to the insoluble phase after the antigen incubation step. After addition of the complex, incubation is carried out for two hours at room temperature. Enzyme activity of the insoluble phase is then determined as previously described.

EXAMPLE IX

The following procedure illustrates the use of competitive binding in quantitating human gamma globulin (IgG).

Using polypropylene tubes coated with rabbit IgG (specific for human IgG), the proper dilution of biotin labeled human IgG for 50% binding is determined by a dilution sequence using 1% horse serum/sodium phosphate buffered saline pH 7.4 as a diluent. A 1:2000 dilution of stock biotin labeled human IgG is found suitable for use.

A dilution series of human IgG is prepared using a human IgG standard (195 mg/100 ml, 22.4 IU/ml). Dilutions ranging from 20 μg/ml to 0.05 μg/ml are prepared by two-fold dilutions of the human IgG standard with a dilution liquid consisting of 1% horse serum of sodium phosphate buffered saline of pH 7.4. To 500 μl of each of thus prepared dilutions is added 500 μl of a 1:2000 dilution of biotin labeled human IgG in 1% horse serum/sodium phosphate buffered saline (PBS)/Tween-20. The resulting dilution mixtures contain a final IgG standard concentration of ½ of the initial dilution to compete with a 1:4000 dilution of the biotin labeled human IgG. Each protein mixture is added to the anti human IgG coated polypropylene tubes in 200 μl aliquots. Two controls are also run using only a 1:4000 dilution of the biotin lableled human IgG and 4% horse serum/PBS/Tween-20. All tubes are capped and incubated at 37° C. for 150 minutes. The reaction solution is aspirated from the tubes which are then washed three times with NaCl-Tween-20. A 1:25 dilution of the stock avidin-HRP complex is 1% horse serum/PBS/Tween-20 is prepared and 200 μl is added to each tube. Incubation is carried out for 1 hour at room temperature. The tubes are aspirated and washed 3 times with NaCl-Tween-20 solution. The enzyme activity of the insoluble phase is then determined by the method described earlier using 1 ml reaction volume.

EXAMPLE X

Human IgE, human alpha$_1$ fetoprotein and human anti-rubella IgG are quantitated in assays using the biotin-avidin system as discussed below.

Preliminary dose response curves were run to establish the proper working ratio of biotin labeled antibody and enzyme labeled avidin.

Human IgE

Human IgE is assayed according to the procedure detailed in Example VIII.

Using anti-IgE coated polypropylene tubes, biotin labeled anti IgE bound to HRP labeled avidin and human IgE, a dose response curve is obtained over the range of 1 IU/ml to 200 IU/ml. The O.D. at 450 nm obtained in the assay is plotted against the log of the IgE concentration in IU/ml. A sigmoidal response curve is obtained with an average coefficient of variation of about 16% for triplicate determinations. In the instant case, maximum incubation time for the biotin labeled anti IgE/HRP labeled avidin complex is 1 hour. Excessive non-specific binding is observed with incubation times exceeding an hour.

Repeating the assay using anti IgE covalently bound to nylon beads as the solid phase gives identical results except the assay gives more rapid color development. For triplicate determinations, the coefficient of variation consistently averages 3% or less.

Human Alpha$_1$ Fetoprotein

Human alpha$_1$ fetoprotein (A$_1$FP) is assayed according to procedures detailed in Examples VII AND VIII.

Using the procedure of Example VII, the dose response curve obtained with biotin labeled anti human alpha$_1$ fetoprotein, HRP labeled avidin and human alpha$_1$ fetoprotein is usable over the range of 1 to 500 ng A$_1$FP/ml when either polypropylene tubes or nylon beads coated with anti human alpha$_1$ fetoprotein are employed as solid phase immuno-adsorbents.

Using the procedure of Example VIII, a similar dose response curve is obtained, however a higher blank value due to non-specific binding reduces the sensitivity of the assay to approximately 5 ng A$_1$FP/ml. This can be overcome by increasing the dilution of the biotin reagent (i.e., biotin labeled anti human alpha$_1$ fetoprotein bound to HRP labeled avidin) and increasing the assay time.

Human Anti Rubella IgG

The detection of Rubella antibodies is accomplished by the following procedure:

Polystyrene microtiter plates, coated with Rubella antigen in 0.1 M sodium carbonate buffer at pH 9.8, are incubated for 3 hours at room temperature with high and low titer Rubella human antisera and negative human control serum. Dilutions ranging from 1:2 to 1:516 are prepared in 4% horse serum/sodium phosphate buffered saline (PBS). The plates are washed 3 times with NaCl-Tween 20 and incubated for 1 hour at room temperature with a pre-mixture of biotin labeled anti human IgG and HRP labeled avidin in 1% horse serum/PBS/Tween-20 at 1:500 and 1:50 dilutions, respectively. After washing, the wells are assayed for enzyme activity with 250 µl of the HRP assay mixture. Qualitatively, the high titer antiserum gives a color response well above the negative control serum over the entire dilution range. The low titer antiserum gives a color response above the negative control serum up to a dilution of 256.

What is claimed is:

1. A method of determining a ligand in a liquid medium suspected of containing same, which method comprises:
   (a) providing an insoluble phase containing a specific binding substance for said ligand;
   (b) incubating said insoluble phase with the following reagents:
      (i) liquid medium suspected of containing said ligand;
      (ii) biotin labeled specific binding substance for said ligand; and
      (iii) enzyme labeled avidin;
   (c) separating unreacted reagents from said insoluble phase after incubation; and
   (d) determining the enzyme activity of either said insoluble phase or separated unreacted reagent whereby said activity is related to the amount of ligand in said liquid medium.

2. A method according to claim 1 wherein step (b) comprises incubating said insoluble phase with reagents (i), (ii) and (iii) in the presence of one another.

3. A method according to claim 1 wherein step (b) comprises incubating said insoluble phase with reagents (i), (ii), and (iii) in the order indicated; step (c) comprises separating unreacted reagent from said insoluble phase after each incubation; and step (d) comprises determining the enzyme activity of either said insoluble phase or separated unreacted enzyme labeled avidin.

4. A method according to claim 1 wherein said ligand is an antigen.

5. A method according to claim 4 wherein said antigen is alpha$_1$ fetoprotein.

6. A method according to claim 1 wherein said ligand is an antibody.

7. A method for determining a ligand in a liquid medium suspected of containing same, which method comprises:
   (a) providing an insoluble phase containing a specific binding substrate for said ligand;
   (b) incubating said insoluble phase with the following reagents:
      (i) liquid medium suspected of containing said ligand; and
      (ii) biotin labeled specific binding substance for said ligand bound to enzyme labeled avidin;
   (c) separating unreacted reagents from said insoluble phase after incubation; and
   (d) determining the enzyme activity of either said insoluble phase or separated unreacted reagent whereby said activity is related to the amount of ligand in said liquid medium.

8. A method according to claim 7 wherein step (b) comprises incubating said insoluble phase with reagents (i) and (ii) in the presence of one another.

9. A method according to claim 7 wherein step (b) comprises incubating said insoluble phase with reagents (i) and (ii) in the order indicated; step (c) comprises separating unreacted reagent from said insoluble phase after each incubation; and step (d) comprises determining the enzyme activity of either said insoluble phase or separated unreacted biotin labeled specific binding substance bound to enzyme labeled avidin.

10. A method according to claim 7 wherein said ligand is an antigen.

11. A method according to claim 10 wherein said antigen is human IgE.

12. A method according to claim 10 wherein said antigen is alpha$_1$ fetoprotein.

13. A method according to claim 7 wherein said ligand is an antibody.

14. A method according to claim 13 wherein said antibody is humann anti-rubella IgG.

15. A method according to claim 14 wherein the specific binding substance contained in said insoluble phase is rubella antigen and the specific binding substance contained in reagent (ii) is anti human IgG.

16. A method for determining a ligand in a liquid medium suspected of containing same, which method comprises:
   (a) providing an insoluble phase containing a specific binding substance for said ligand;
   (b) incubating said insoluble phase with the following reagents:
      (i) (A) liquid medium suspected of containing said ligand and (B) a known quantity of biotin labeled ligand; and
      (ii) enzyme labeled avidin;
   (c) separating unreacted reagents from said insoluble phase after incubation; and
   (d) determining the enzyme activity of either said insoluble phase or separated unreacted reagent whereby said activity is related to the amount of ligand in said liquid medium.

17. A method according to claim 16 wherein step (b) comprises incubating said insoluble phase with reagents (i) and (ii) in the presence of one another.

18. A method according to claim 16 wherein step (b) comprises incubating said insoluble phase with reagents (i) and (ii) in the order indicated; step (c) comprises separating unreacted reagent from said insoluble phase after each incubation; and step (d) comprises determining the enzyme activity of either said insoluble phase or separated unreacted enzyme labeled avidin.

19. A method according to claim 16 wherein said ligand is an antigen.

20. A method according to claim 19 wherein said antigen is human IgG.

21. A method according to claim 16 wherein said ligand is an antibody.

22. A method for determining a ligand in a liquid medium suspected of containing same, which method comprises:
   (a) providing an insoluble phase containing a specific binding substance for said ligand;
   (b) incubating said insoluble phase with a reagent comprising (A) liquid medium suspected of containing said ligand and (B) a known quantity of biotin labeled ligand bound to enzyme labeled avidin;
   (c) separating unreacted reagent from said insoluble phase after incubation; and
   (d) determining the enzyme activity of either said insoluble phase or separated unreacted reagent whereby said activity is related to the amount of ligand in said liquid medium.

23. A method according to claim 22 wherein said ligand is an antigen.

24. A method according to claim 22 wherein said ligand is an antibody.

25. A method according to claims 1, 2, 3, 4, 5 or 6 wherein said insoluble phase, said biotin labeled specific binding substance and said enzyme labeled avidin are each present during incubation in excess of the total amount of ligand in the liquid medium.

26. A method according to claims 7, 8, 9, 10, 11, 12, 13, 14, or 15 wherein said insoluble phase and said biotin labeled specific binding substance bound to enzyme labeled avidin are each present during incubation in excess of the total amount of ligand in the liquid medium.

27. A method according to claims 16, 17, 18, 19, 20 or 21 wherein said ligand to be determined, said biotin labeled ligand and said enzyme labeled avidin are each present during incubation in excess of said insoluble phase, the quantity of biotin labeled ligand not exceeding the smallest quantity of ligand to be determined in the liquid medium.

28. A method according to claims 22, 23 or 24 wherein said ligand to be determined and said biotin labeled ligand bound to enzyme labeled avidin are each present during incubation in excess of said insoluble phase, the quantity of biotin labeled ligand bound to enzyme labeled avidin not exceeding the smallest quantity of ligand to be determined in the liquid medium.

* * * * *